United States Patent [19]

Livny

[11] Patent Number: 4,964,858
[45] Date of Patent: Oct. 23, 1990

[54] ORTHOPEDIC DIAPER DEVICE

[75] Inventor: Michael Livny, Mevasseret, Israel

[73] Assignee: Advanced Computerized Systems Medical, Ltd., Jerusalem, Israel

[21] Appl. No.: 293,504

[22] Filed: Jan. 4, 1989

Related U.S. Application Data

[63] Continuation-in-part of Ser. No. 188,632, May 2, 1988, abandoned, which is a continuation-in-part of Ser. No. 29,659, Mar. 24, 1987, abandoned.

[30] Foreign Application Priority Data

Jan. 26, 1987 [IL] Israel .................................... 81390

[51] Int. Cl.$^5$ ............................................. A61F 13/16
[52] U.S. Cl. ............................... 604/385.1; 128/87 C; 128/DIG. 20
[58] Field of Search ..................... 604/385.1, 380, 350; 128/87 C, 80 A, DIG. 20

[56] References Cited

U.S. PATENT DOCUMENTS

| 2,935,984 | 5/1960 | Kerr . | |
|---|---|---|---|
| 3,834,376 | 9/1974 | Thum | 128/80 A |
| 4,108,168 | 8/1978 | Craig | 128/87 C X |
| 4,393,865 | 7/1983 | Lambert . | |

FOREIGN PATENT DOCUMENTS

| 1491199 | 4/1969 | Fed. Rep. of Germany . |
| 3316903 | 11/1983 | Fed. Rep. of Germany . |
| 2050637 | 4/1971 | France . |

Primary Examiner—Richard J. Apley
Assistant Examiner—Rachel M. Healey
Attorney, Agent, or Firm—Bernard, Rothwell & Brown

[57] ABSTRACT

An inflatable cushion forming an orthopedic device for being affixed on the face of the diaper away from an infant's body at the groin between the thighs for supporting the thighs in an abducted position. The inflatable cushion can be affixed by attachment with adhesive strips, by insertion in a pocket, by being formed integrally, or by otherwise being attached to the diaper or a baby panties covering the diaper.

20 Claims, 9 Drawing Sheets

ORTHOPEDIC DIAPER DEVICE

CROSS-REFERENCE TO RELATED APPLICATIONS

This application is a continuation-in-part of my application Ser. No. 188,632, filed May 2, 1988, now abandoned, which was a continuation-in-part of my application Ser. No. 29,659, filed Mar. 24, 1987, now abandoned. These applications are hereby incorporated herein in their entirety.

BACKGROUND OF THE INVENTION

The present invention is directed to an inflatable device suitable for the treatment or prevention of a congenital defect, congenital dislocation or dysplasia of the hip joint, in both diagnosed and undiagnosed cases, immediately or shortly after birth.

There is some confusion in the use of these terms, since dysplasia means only a dislocatable hip joint, and a distinction is important when considering the incidence of the defect. On the average, according to some authorities, the incidence of dysplasia seems to be about one percent of live births, but the fully developed cases of dislocated hips are considerably less frequent. This lends some authorities to the conclusion that there is a possibility of spontaneous stabilization of dysplastic hips in early infancy, even when not treated.

In any case, where there is only mild dysplasia it is not always diagnosed even by trained personnel, especially during early infancy. Therefore, it is possible that a number of cases may go undetected until the child is two or three months old, when X-ray examination will provide conclusive proof of whether there is a dysplasia/dislocation or not. The presence of such abnormalities calls for treatment by immobilization with appropriate splints, usually keeping the legs abducted at approximately 60° and appropriately flexed. This posture which allows the head of the femur to exert pressure on the acetabulum (socket) has been proven to enhance good development as well as stabilization of the hip joint.

An adducted position of the thighs in infancy may lead to a higher incidence of dysplastic, respectively dislocated hips. This is supported by observations of such a higher incidence in populations where it is customary to swaddle infants with thighs in an adducted position. The importance of holding the thighs in an abducted position is now well recognized, and the present widespread practice is to use a makeshift arrangement, i.e., to use two, or perhaps more, layers of diapers, providing some semi-rigidity and also a kind of wad in the region of the groin to achieve abduction. However, this practice is only partially effective as the material of the diapers is water absorbent and loses almost all rigidity and resistance on becoming wet. Furthermore, it involves additional work, expense, and inconvenience.

Splints are used in the therapeutical treatment of diagnosed cases, but these are very rigid splints which tend to bruise the delicate skin of an infant. The use of foamed plastic cushions, trapped to the thighs and permitting certain freedom of adductive movements but capable of recovering their shape, has also been recommended in the literature.

SUMMARY OF THE INVENTION

The present invention contemplates only non-water absorbent means for holding the thighs of the infant in the abducted position, the problem of becoming ineffective in the wet state does not arise, and this constitutes a considerable advantage of the present invention over the prior art makeshift solutions.

Therefore, the present invention provides an orthopedic device for infants characterized in that it comprises an inflatable cushion integral with a diaper, appropriately insertable into a diaper, or adapted to be positioned on a diaper; said cushion being non-water absorbent and being located in the set-up position of the diaper, at the groin, between the thighs and supporting them in an abducted position. Several embodiments are suitable for realizing the present invention.

It seems to be desirable to avoid use of relatively hard and overly rigid materials, which may bruise the delicate skin of the infant. Therefore, inflated cushions provide sufficient rigidity for holding the thighs in the desired abducted position with minimum risk for bruising the skin of the infant.

Since most modern mothers are disinclined to launder diapers, the embodiment involving disposable diapers will be most common at present, but the invention may be equally well applied to reusable fabric diapers which may be more economical in some cases. Of course, in case of reusable diapers, the embodiment involving separate insertable means is preferable, as diapers integrally incorporating said means may be inconvenient to launder.

In the case of using separate insertable means, these are held in appropriate pockets, integrally formed with the diaper proper.

BRIEF DESCRIPTION OF THE DRAWINGS

Embodiments of the present invention are shown in detail in the accompanying drawings wherein.

DETAILED DESCRIPTION OF THE PREFERRED EMBODIMENTS

Figure 1:
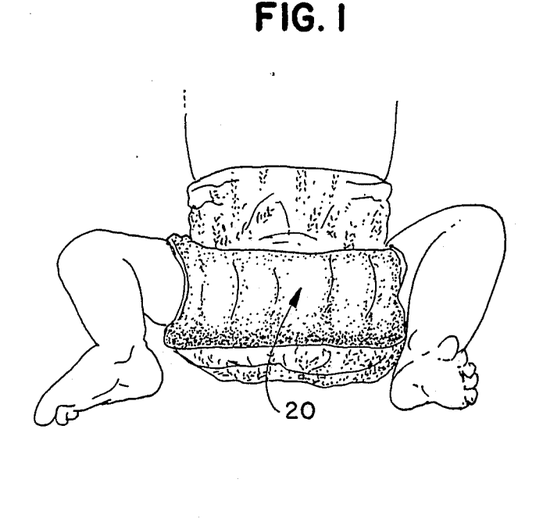
FIG. 1 represents a general view of an infant wearing a diaper with an inflatable cushion in accordance with the invention.

FIG. 1 is a schematic general view, mainly to visualize the position the infant's thighs assume when wearing a diaper in accordance with the present invention with an air cushion supporting the thighs indicated generally by an arrow 20. The diaper may be either a disposable diaper or a reusable fabric diaper. The air cushion is simply affixed to the outermost layer of the diaper, which may be done by a suitable adhesive, by heat-sealing the cushion to the diaper, by forming the air cushion from double outer layers of the diaper, by holding the air cushion in place by an additional outer layer pocket in the diaper, by affixing the air cushion to a baby panties which holds the air cushion in place over the diaper, or by any other conventional affixing manner.

Figure 2:
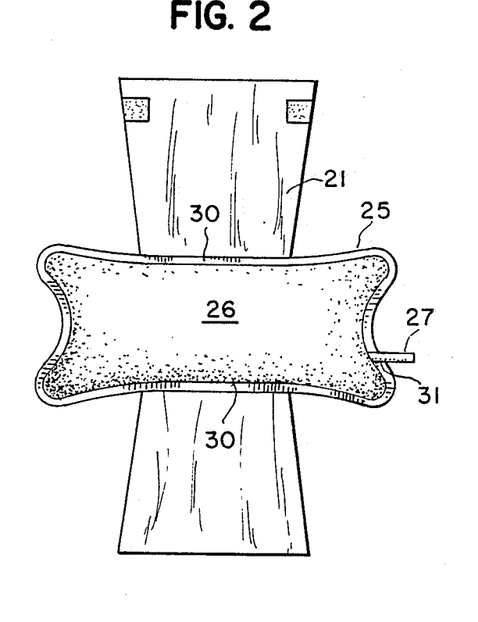
FIG. 2 is a plan view of one embodiment of the diaper of FIG. 1 in an unfolded condition.
Figure 3:
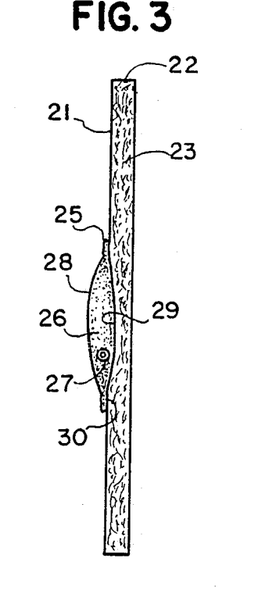
FIG. 3 is a side view of the diaper of FIG. 2.

In the embodiment of FIGS. 2 and 3 an inflatable air cushion 26 is affixed on the side of a non-absorbent layer 21 on the side of the diaper which faces away from the infant's body.

The air cushion 26 is formed from thermoplastic film sheets 28 and 29 heat sealed together at 25. The diaper has a water impermeable layer such as thermoplastic film layer 21, an absorbing layer 22 and a permeable tissue layer 23 facing the body of the infant. The cushion 26 has portions 30 of the heat sealed edges 25 heat sealed or adhesively attached to the diaper layer 21. A suitable free opening 31 for inflating the inflatable cushion 26 is formed between layers 28 and 29 in the area delimited by said heat sealing line 25. A short length of tubing 27 containing a self-sealing valve may be inserted in said opening, or a tubing may be formed by suitably extending said heat sealable layers from the cushion 26 and appropriately configuring the heat sealing line.

The inflating may be done by mouth or by a small aerosol containing a suitable gas. Also the inflation may also be done by a gas-producing mixture of chemicals.

Figures 4, 5, 6:
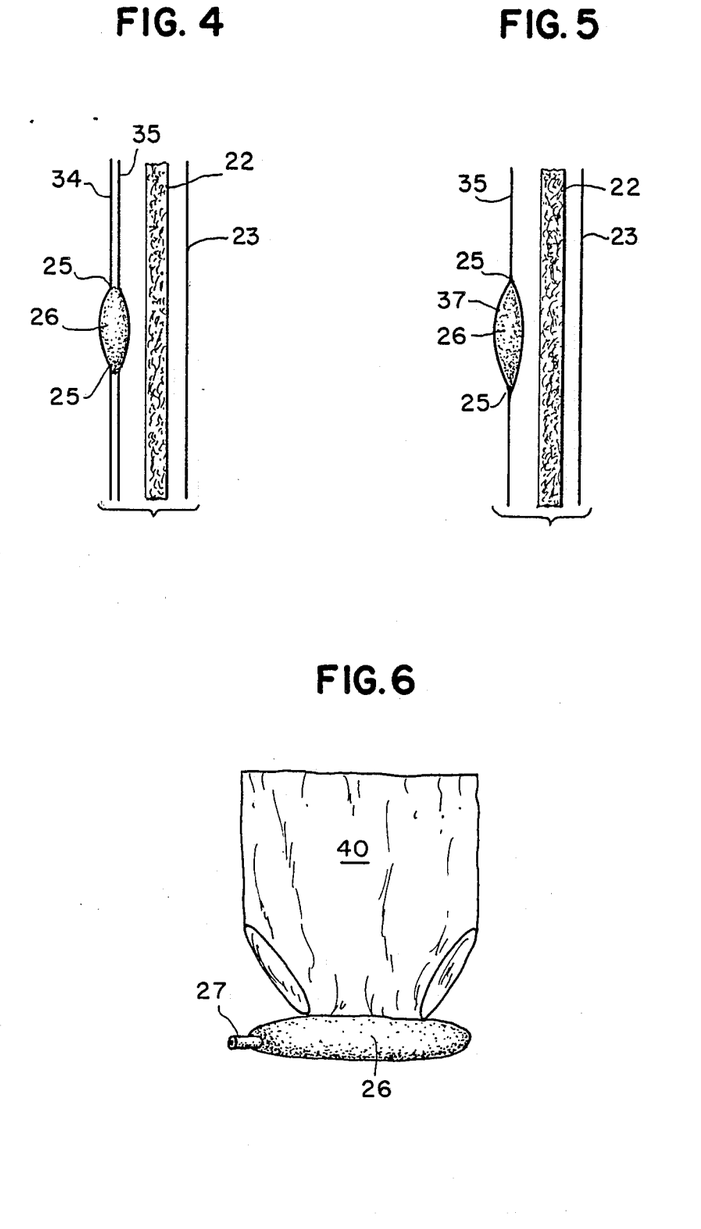
FIG. 4 is an exploded side view of a variation of the embodiment of FIGS. 2 and 3.
FIG. 5 is a view similar to that of FIG. 4 showing another variation of the embodiment of FIGS. 2 and 3.
FIG. 6 is a front view of an inflatable cushion on a baby panties according to still another variation of the present invention.

In a variation shown in FIG. 4, 34 and 35 designate two heat sealable plastic layers forming the nonabsorbent layer on the outermost side of the absorbing layer 22. These two layers are heat-sealed together along line 25 forming the cushion 26.

In the variation illustrated in FIG. 5 there is only one layer 35 of plastic sheet covering most of the surface of the diaper and a second layer 37, is heat-sealed to the layer 35 only in the region forming the inflatable cushion 26.

Figure 7:
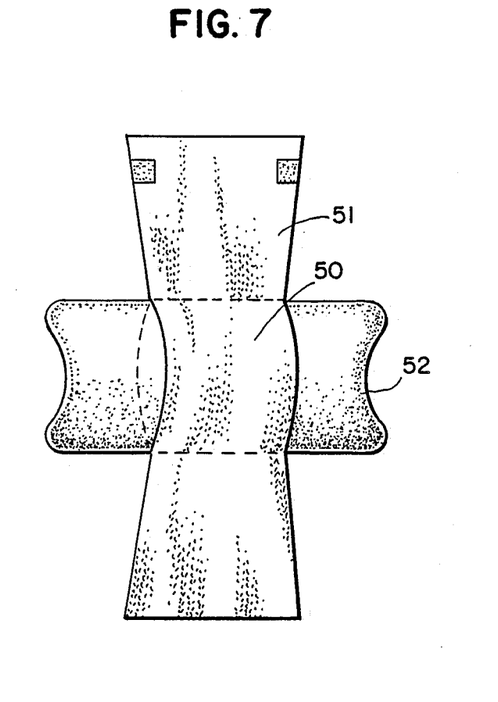
FIG. 7 is a plan view of a modified diaper and inflatable cushion in accordance with the invention.
Figure 8:
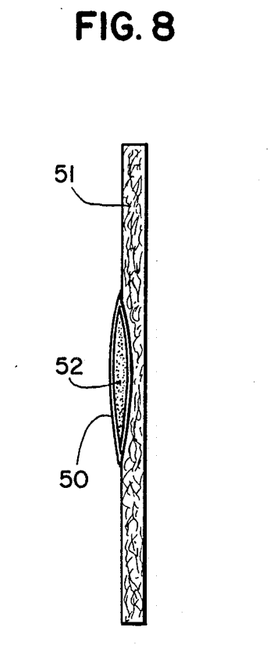
FIG. 8 is a left side view of the diaper and cushion of FIG. 7.
Figure 9:
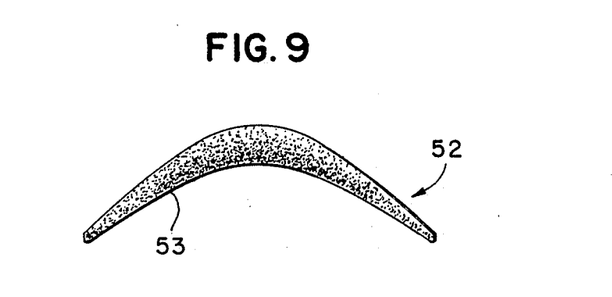
FIG. 9 is a side view of the air cushion taken from the bottom of FIG. 7.

The embodiment illustrated in FIGS. 7 and 8 may be used either with a disposable or with a reusable fabric diaper. A pocket 50 is formed on the side of diaper 51 facing away from the infant's body, the pocket may be open at both sides or only at one side and is adapted for insertion thereinto of an air cushion 52 having adequate elasticity and stiffness. The cushion 52 has a concave face 53 facing away from the infant's body. Of course, the cushion 52 may be an inflatable cushion similar to the inflatable cushion 26 of FIG. 2.

An additional variation of the invention shown in FIG. 6 relates to baby panties comprising an inflatable cushion on the face of the panties facing away from the infant's body, integral with the same, or appropriately insertable thereinto or affixed thereto, said cushion being non-water absorbent and being located at the groin, between the thighs and supporting the same in an abducted position. Baby panties 40 is equipped with cushion 26, which is provided with inflating tube 27. The cushion 6 may be either integrally formed with the panties, in a manner parallel to that described for the diaper, illustrated in FIGS. 4 and 5. Alternatively, a cushion according to FIG. 5 may be affixed to the panties on the outer side thereof such as shown in FIGS. 2 and 3 or FIGS. 7 and 8 for a diaper.

Figure 10:
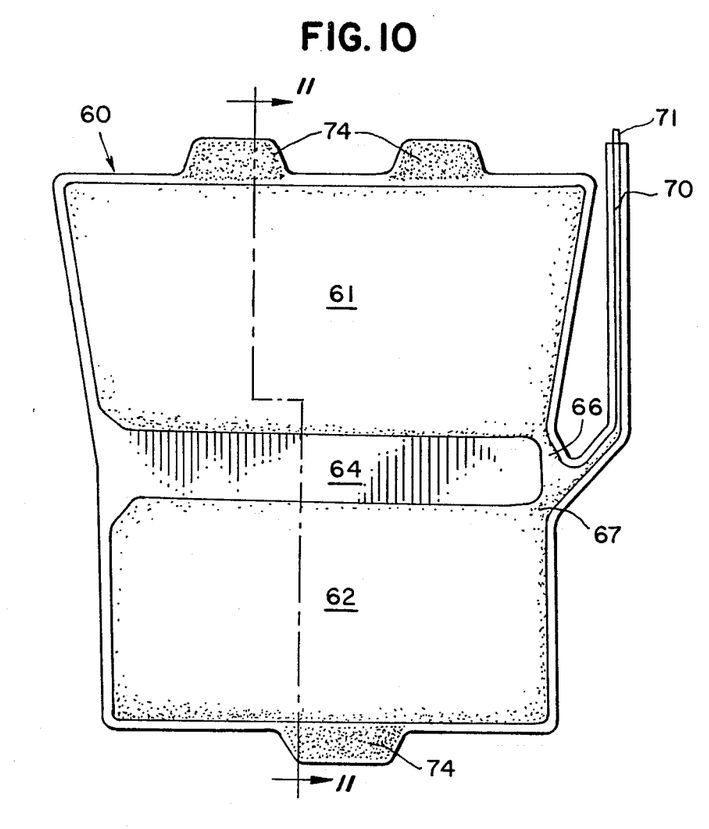
FIG. 10 is a plan view of an inflatable cushion for use with a diaper in accordance with another embodiment of the present invention.
Figure 11:
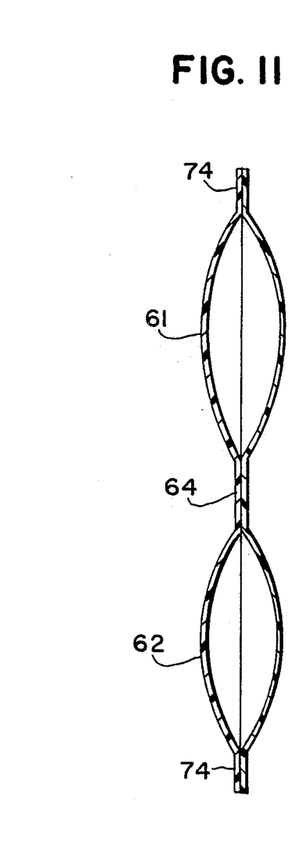
FIG. 11 is a cross-section view of the cushion of FIG. 10 taken along the line 11—11, when inflated.

A modified inflatable cushion 60 illustrated in FIGS. 10 and 11 is made from suitable heat sealed plastics material, and has a front inflatable part 61 and a rear inflatable part 62. The two parts 61 and 62 are practically separated from each other by a heat-sealed strip 64, extending through almost the whole width of the cushion, leaving inlets 66 and 67, to allow for inflating. The strip 64 serves as the folding axis of the cushion. An inflating tube 70 is integrally formed with the cushion, as is seen in FIG. 10. The inflating tube 70 can be further equipped with a pipe 71, which enables easier inflating.

Figure 12:
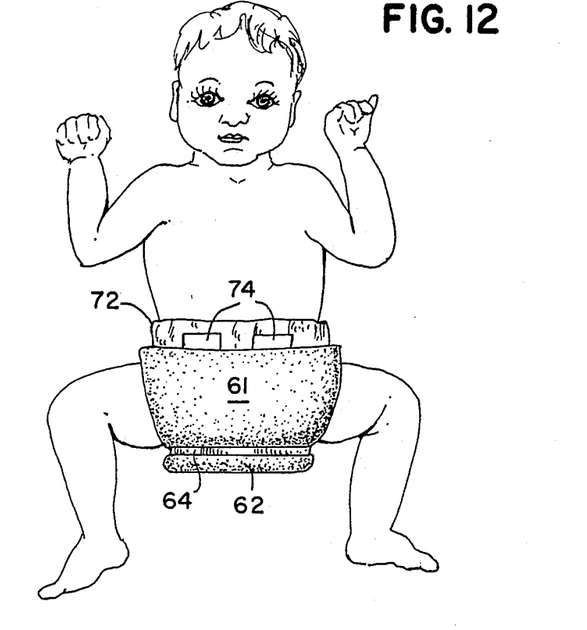
FIG. 12 is a front view of a child wearing a diaper with the inflatable cushion of FIGS. 10 and 11 affixed thereto.
Figure 13:
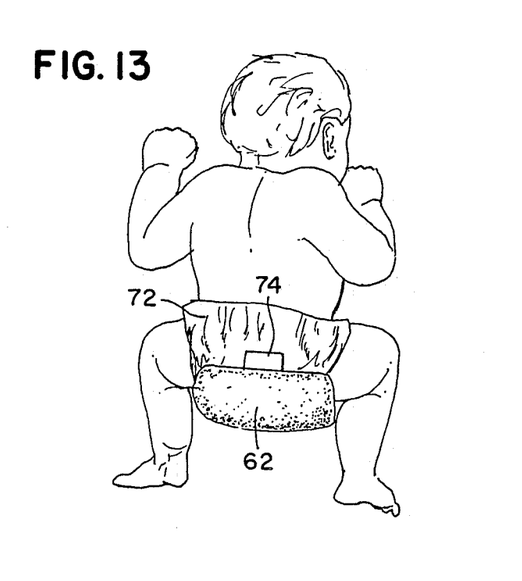
FIG. 13 is a rear view of the infant, diaper and inflatable cushion of FIG. 12.
Figure 14:
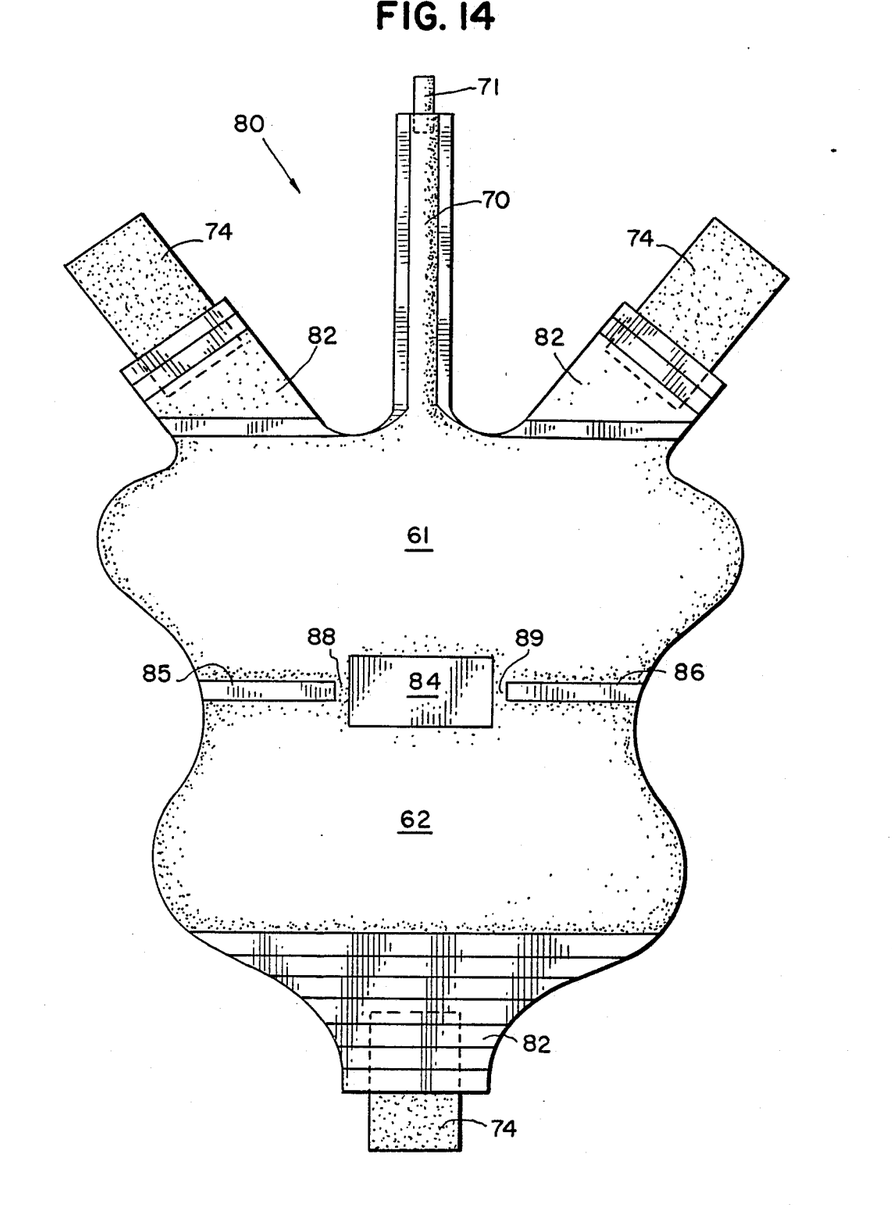
FIG. 14 is a plan view of a further modified inflatable cushion for attachment to a diaper in accordance with the invention.

The cushion may be inflated completely or partially until desired pressure or firmness is achieved empirically. The tube 70 is securely tied around itself to prevent escape of air. The cushion is then affixed to a diaper 72, either before or after putting the diaper on the baby, by adhesive tapes 74. This is illustrated in FIGS. 12 and 13.

Figure 15:
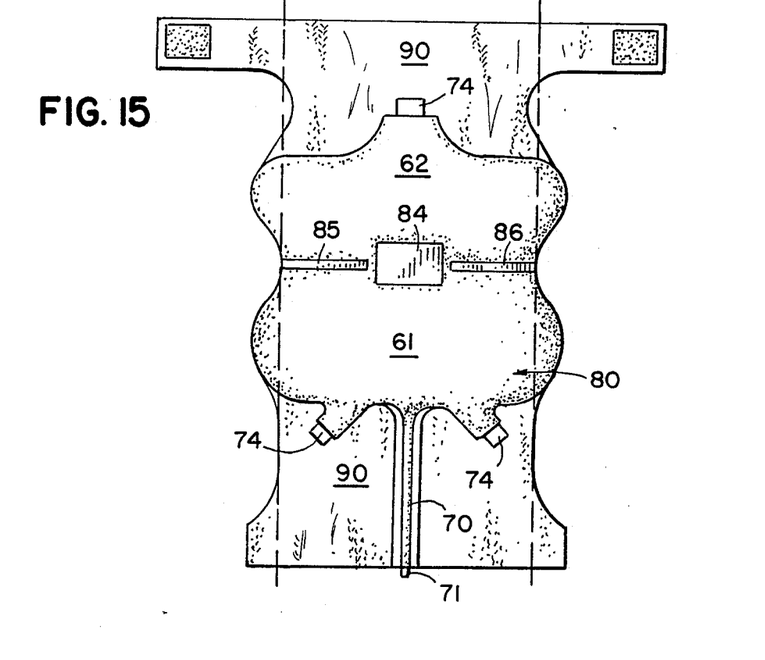
FIG. 15 is a plan view showing the inflatable cushion of FIG. 14 attached to a diaper or baby panties.
Figure 16:
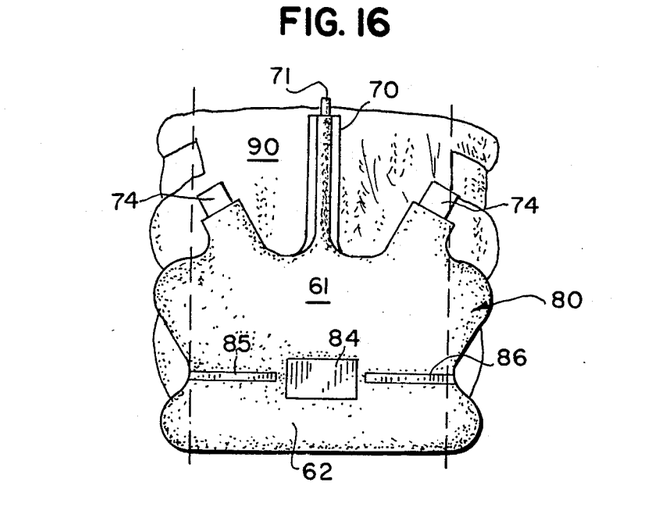
FIG. 16 is a front view of the inflatable cushion and diaper or panties of FIG. 15 in a set-up position.
Figure 17:
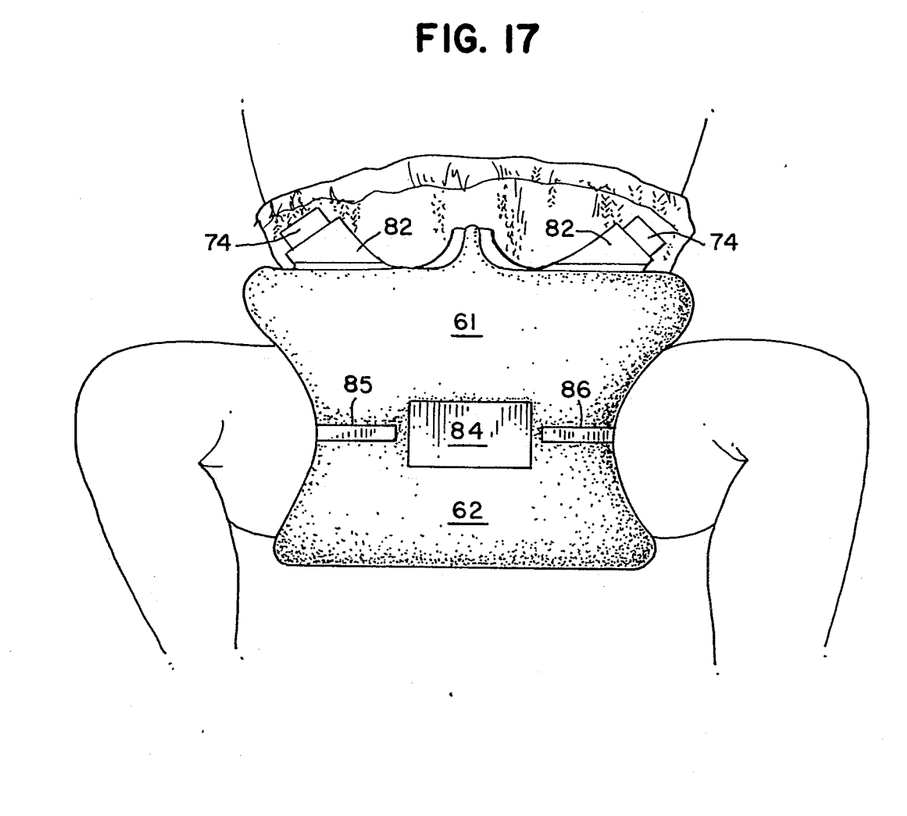
FIG. 17 is a front view showing the inflatable cushion and diaper or panties of FIG. 15 on an infant.

A further modified inflatable air cushion 80 is shown in FIGS. 14–17. The front and rear inflatable parts 61 and 62 are contoured to fit around an infant's legs, see FIG. 17. The inflation tube 70 extends from the upper front edge so that it may be folded and tucked under the cushion. Tab portions 82 are formed by heat-sealed strips to provide a more secure base for attachment of the adhesive strips 74. Separation of the front and rear portions 61 and 62 is provided by enlarged center heat-sealed portion 84 and side heat seal strips 85 and 86 with unsealed passages 88 and 89 providing communication between the front and rear cushion portions 61 and 62. FIGS. 15 and 16 show the releasable affixation of the cushion 80 by the adhesive strips 74 to a diaper or baby panties 90 in the open and set-up positions, respectively.

Figure 18:
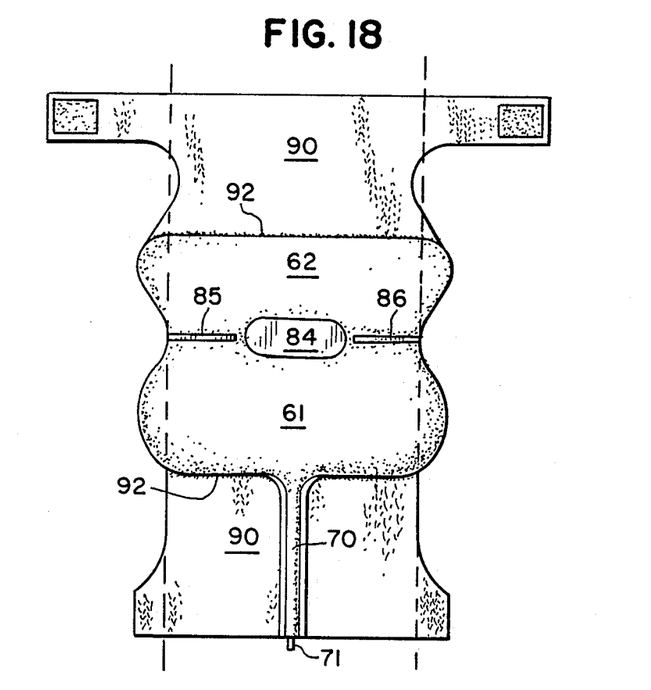
FIG. 18 is a view similar to FIG. 15 but of an inflatable cushion permanently affixed or integrally formed with a diaper or baby panties.
Figure 19:
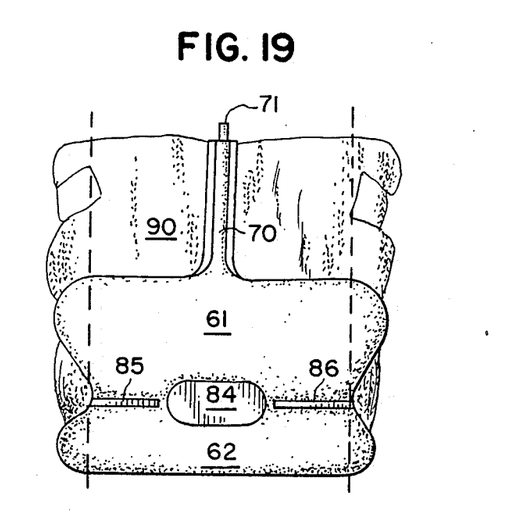
FIG. 19 is a front view of the inflatable cushion and diaper or panties of FIG. 18 in a set-up position.

In a variation shown in FIGS. 18 and 19 of the modified diaper with orthopedic cushion of FIGS. 14–17, the cushion portions 61 and 62 are permanently affixed at 92, or integrally formed, with the diaper or baby panties 90.

While several specific embodiments have been described hereinabove in detail, the invention is not limited thereto and is only defined by the scope of the appended claims.

It is claimed:

1. A diaper for infants comprising an absorbing layer, and an inflatable cushion for being positioned on the face of the diaper away from the infant's body, said cushion being non-water absorbent and being located, in the set-up position of the diaper, at the groin, between the thighs for supporting them in an abducted position.

2. A diaper according to claim 1 wherein said diaper is a disposable diaper.

3. A diaper according to claim 1 wherein the diaper comprises two layers of water-impermeable heat-sealable plastic sheets on the side facing away from the infant's body and said inflatable cushion is formed by heat-sealing said sheets together along a line in the region between the thighs leaving a closable opening for inflating said cushion.

4. A diaper according to claim 1 wherein the diaper comprises one layer of water impermeable, heat-sealable plastic sheet on the side facing away from the infant's body, a second layer of water impermeable, heat-sealable plastic sheet being heat-sealed to said plastic sheet in the region of said inflatable cushion between the thighs, leaving a closable opening for inflating said cushion.

5. A diaper according to claim 1 wherein the cushion is formed integral with the absorbing layer.

6. A diaper according to claim 1 including adhesive strips for securing the inflatable cushion on the face of the diaper.

7. A diaper according to claim 1 including a baby panties for being positioned on the face of the diaper, and means for positioning the inflatable cushion on the baby panties.

8. A diaper according to claim 7 wherein the cushion is formed integral with the baby panties.

9. A diaper according to claim 7 including adhesive strips for securing the inflatable cushion on the face of the baby panties.

10. A diaper comprising an absorbent layer and means having an open pocket in the region between the thighs, said pocket being adapted for insertion thereinto of an inflatable cushion of non-water absorbent material for supporting the thighs, in an abducted position.

11. A diaper according to claim 10 wherein said pocket is formed by a sleeve, open at both ends thereof.

12. An orthopedic device for treatment of dysplasia of a hip joint of an infant, comprising an inflatable cushion, and means for securing the cushion on the face of a diaper away from the infant's body, said cushion being non-water absorbent and being located, when in the inflated condition on the diaper, at the groin, between the thighs of the infant for supporting the thighs in an abducted position.

13. An orthopedic device according to claim 12 wherein the inflatable cushion includes a front inflatable part, a rear inflatable part, and a strip separating the front and rear inflatable parts.

14. An orthopedic device according to claim 12 including an inflating tube integrally formed with the cushion.

15. An orthopedic device according to claim 13 including an inflating tube integrally formed with the cushion at one end of the strip and having a pair of inlets communicating with the respective front and rear inflatable parts.

16. An orthopedic device according to claim 12 wherein the securing means includes adhesive strips for securing the cushion on the diaper.

17. An orthopedic device according to claim 12 wherein the securing means includes a baby panties.

18. An orthopedic device according to claim 17 wherein said inflatable cushion is formed integral with said panties.

19. An orthopedic device according to claim 13 including an inflating tube integrally formed with the front inflatable part, and having passage means formed through the strip to communicate between the front and rear inflatable parts.

20. An orthopedic device according to claim 16 wherein the securing means includes tabs formed integral with the cushion for being attached by the adhesive strips to the diaper.

* * * * *